United States Patent [19]

Bergink

[11] Patent Number: 5,262,408
[45] Date of Patent: Nov. 16, 1993

[54] LOW ESTROGEN ORAL CONTRACEPTIVES

[75] Inventor: Engelhart W. Bergink, Oss, Netherlands

[73] Assignee: Akzo N.V., Arnhem, Netherlands

[21] Appl. No.: 806,966

[22] Filed: Dec. 12, 1991

[30] Foreign Application Priority Data

Dec. 13, 1990 [EP] European Pat. Off. ......... 90203309.1

[51] Int. Cl.$^5$ ............................................. A61K 31/56
[52] U.S. Cl. .................... 514/182; 514/170; 514/179; 514/843
[58] Field of Search ................ 514/170, 179, 182, 843

[56] References Cited

U.S. PATENT DOCUMENTS

| | | | |
|---|---|---|---|
| 4,378,356 | 3/1983 | de Jager et al. | 424/238 |
| 4,544,554 | 10/1985 | Pasquale | 514/170 |
| 4,616,006 | 10/1986 | Pasquale | 514/170 |
| 4,628,051 | 12/1986 | Pasquale | 514/170 |

FOREIGN PATENT DOCUMENTS

0253607  1/1988  European Pat. Off. .

OTHER PUBLICATIONS

CA 114:88652v, De Jager, 1990.

*Primary Examiner*—Frederick E. Waddell
*Assistant Examiner*—Kimberly R. Jordan
*Attorney, Agent, or Firm*—William M. Blackstone

[57] ABSTRACT

Disclosed is a contraceptive regimen, and method of using the regimen, comprising 24 daily sequential dosage units of: a first phase comprising about 7 to 9 separate first dosage units containing a progestogen at a daily dosage equivalent in progestogenic activity to 100 desogestrel and an estrogen at a daily dosage equivalent in estrogenic activity to 25 μg ethinyl estradiol ("EE"). A second phase of 7 to 9 second dosage units, each of the second dosage units containing a progestogen equivalent to 125 μg desogestrel and an estrogen equivalent lent to 20 μg EE. A third phase of 7 to 9 third dosage units, each unit containing a progestogen equivalent to 50 μg desogestrel and an estrogen equivalent to 20 μg EE. The kit generally has 28 daily dosage units wherein four of the daily dosage units contain no contraceptive steroid, or, alternatively, have only 24 dosage units with a four day "pill-free" period. The fourth phase may also be four dosage units containing a progestogen equivalent to 25-35 μg desogestrel.

9 Claims, No Drawings

LOW ESTROGEN ORAL CONTRACEPTIVES

TECHNICAL FIELD

The invention relates generally to oral contraceptive preparations, and more specifically to a low estrogen oral contraceptive regimen.

BACKGROUND ART

Since the first birth control pill regimen was described, attempts have been made to lower the total steroid dosage in the regimen, while maintaining the regimen's reliability in providing contraception.

For example, U.S. Pat. No. 4,628,051 to Ortho Pharm. Corp. discloses a three phase oral contraceptive containing estrogen and progestogen for administration over 21 days having a lower total monthly steroid dose having the same amount of estrogen in each phase. In the first phase, 5 to 8 tablets containing 0.02 to 0.05 milligrams (mg) ethinyl estradiol ("EE") and 0.065 to 0.75 mg of norethindorone ("NE") are administered daily. In the second phase, 7 to 11 tablets containing the same dosage of EE and 0.25 to 1 mg of NE are administered. In the third phase, 3 to 7 tablets containing the same dosage of EE and 0.35 to 2 mg of NE are administered. While an adequate contraceptive regimen, a 7 day pill free interval can lead to follicular development and thus pregnancy. Furthermore the preferred and described regimens administer 0.735 mg of EE, which to some is considered too large a dosage. Similar regimens are described in U.S. Pat. Nos. 4,616,006, 4,544,554, and 4,530,839 also to Ortho Pharm. Corp.

West German patent application no. 3,341,638 to Hesslinger discloses another triphasic contraceptive regimen wherein contraceptive pills are administered over 22 days. The first phase of this regimen contains 6 pills having 30 µg EE and 0.75 mg lynestrenol. The second phase contains 5 pills having 40 µg EE and 1.0 mg lynestrenol. The third phase contains 11 pills having 30 µg EE and 1.5 mg lynestrenol. This results in a total estrogen dose of 710 µg of EE per cycle.

Another attempt to decrease estrogen levels in triphasic contraceptive regimens is described in Belgian patent 823,689 to Schering AG. In this contraceptive regimen of 21 pills, the first phase consists of 4 to 6 pills containing a first dose of estrogen (e.g. 30 µg EE) and a first dose of progestogen (e.g. 50 µg D-norgestrel). The second phase contains 4 to 6 pills containing one to two times the estrogen dose and one to one and a half times the progestogen dose of the first phase. The third phase contains 9 to 11 pills containing the same or a lesser amount of estrogen as the pills of the first phase, and up to three times the amount of progestogen. A very similar regimen is described in DE 3,347,125, also to Schering AG. Again, the 7 day pill free interval can lead to follicular development and thus pregnancy.

Another patent application of Schering AG (DT 2,645,307) describes a 28 day, 3 stage treatment for treating climacteric disorders. A 28 to 32 day steroid regimen, used in establishing cyclicity in human females, is disclosed in U.S. Pat. No. 3,639,600 to Upjohn wherein 2.550 mg of EE is administered over the treatment period.

DT 2,431,704 to Asche CF & Co. AG discloses a triphasic contraceptive where, in the first stage, a low dose of estrogen (e.g. 0.030 mg EE) and a progestogen (e.g. 1.00 mg norethisterone acetate) are administered for 6 to 8 days; in the second stage, a slightly increased ($\leq$2-fold) dose of estrogen and slightly increased ($\leq$1.5-fold) dose of progestogen are administered for 6 to 8 days; and, in the third stage, an estrogen dose no higher than the second stage, and an increased ($\leq$3-fold of the first stage) progestogen dose are administered for 6 to 8 days. At the very least, 630 g of EE is still administered in this particular regimen.

South African patent 8509-892-A to Warner Lambert Co. describes a three or four phase oral contraceptive regimen having a relatively high amount of norethindrone acetate (i.e. from 0.5 to 1.5 mg) and relatively low amount of EE (10 to 50 µg) or other estrogenic substance. The four phase regimen is administered over a 23 to 34 day cycle having an inactive phase.

European Patent application 253,607 to American Home Prods. discloses a mono-phasic contraceptive preparation containing 23 to 25 dosage units having 0.008 to 0.030 mg of EE in combination with 0.025 to 0.100 mg of desogestrel which is administered over 23 to 25, preferably 24, days followed by a 2 to 5 day pill-free period.

Still another attempt to minimize estrogen levels in sequential oral contraceptives is disclosed in Dutch patent application 6911920 to Unisearch Ltd. This patent application describes a pack containing at least 28 pills, 25 to 27 of which are active. Of the active pills, 17 to 20 are estrogen only (e.g. ethinyl estradiol) pills, with the remainder containing both an estrogen and a progestogen. The low estrogen pills contain 0.050 to 0.080 mg of an estrogen, while the high estrogen pills contain 0.07 to 0.08 mg estrogen. The combination pills contain 0.07 to 0.12 mg estrogen and 0.8 to 1.4 mg of progestogen. Even with this minimized estrogen contraceptive, at least 1.610 mg of estrogen are administered, while in the preferred embodiment, 1.950 mg are administered.

European patent application no. 36,229 to Akzo, nv discloses a multiphase combination-type sequential oral contraceptive consisting of 20 to 22 tablets each containing a progestogen and an estrogen. The first phase contains a relatively low dose of progestogen (e.g. less than 50 micrograms of desogestrel), followed by phases containing more progestogen (e.g. 100 µg and 200 µg desogestrel in the second and third phases, repsectively).

A need exists for an effective low dose contraceptive regimen having the benefits of multiphasic administration (e.g. ideal cycle control), while still preventing follicular development during the pill-free interval.

DISCLOSURE OF THE INVENTION

It has been found that by properly selecting, at a low level, the dosage of the estrogen component in a multiphasic contraceptive regimen, and administering it over 24 days, while at the same time slowly and incrementally increasing the progestogen administered, a highly reliable contraceptive regimen having low doses of both estrogen and progestogen is attained.

The invention thus includes a multiphasic combination and contraceptive kit containing at least three phases. These three phases consist of 24 daily sequential daily dosage units, i.e. a first phase having 7 to 9 separate first dosage units, the first dosage units containing a progestogen at a daily dosage equivalent in progestogenic activity to 75 to 100 micrograms desogestrel and an estrogen at a daily dosage equivalent in estrogenic activity to 25 micrograms ethinyl estradiol. The second phase has 7 to 9 second dosage units, each of the second dosage units containing a progestogen at a daily dosage equivalent in progestogenic activity to 100 to 125 micrograms desogestrel and an estrogen at a daily dosage equivalent in estrogenic activity to 20 micrograms ethinyl estradiol. The third phase has 7 to 9 third dosage units, each of the third dosage units containing a progestogen at a daily dosage equivalent in progestogenic activity to 125 to 150 micrograms desogestrel and an estrogen at a daily dosage equivalent in estrogenic activity to 20 micrograms ethinyl estradiol.

The kit will generally have 28 daily dosage units (i.e. include a fourth phase) wherein four of the daily dosage units contain no contraceptive steroid (e.g. are "blanks" or placebos or contain iron). Alternatively a four day "pill-free" period may be utilized, or the fourth phase may also be four daily dosage units containing a progestogen at a daily dosage equivalent in progestogenic activity to 25 to 35 micrograms desogestrel.

The invention also includes a contraceptive product (i.e. the birth control pack containing the dosage unit regimen), and a process of manufacturing this product.

BEST MODE OF THE INVENTION

Preferred progestogens for use with the invention include 3-ketodesogestrel ("etonogestrel"), desogestrel, levo-norgestrel, norgestrel, gestodene, and other compounds with similar progestogenic activity. Especially preferred are 3-ketodesogestrel and desogestrel. As an approximation, levo-norgestrel, desogestrel, and 3-ketodesogestrel are relatively equipotent in progestogenic activity. Gestodene is approximately 1.5 times as potent as these compounds. Norgestrel is about one-half as potent as levo-norgestrel.

Examples of preferred estrogens include 17$\beta$-estradiol and ethinyl estradiol. Mestranol and 17-$\alpha$-ethinyl estradiol 3-methylether are also useful estrogens. As an approximation, 1 mg of 17$\beta$-estradiol is equivalent in estrogenic activity to 0.015 mg of ethinyl estradiol and 0.030 mg of mestranol.

The estrogen and progestogen ("contraceptive steroids"), or either of them are incorporated into dosage units for oral administration. The term "dosage unit" generally refers to physically discrete units suitable as unitary dosages for humans or animals, each containing a predetermined quantity of active material (e.g. estrogen or progestogen) calculated to produce the desired effect.

Methods and compositions for making such dosage units are well-known to those skilled in the art. For example, methods and compositions for making tablets and pills, containing active ingredients, are described in the standard reference, Chase et al., *Remington's Pharmaceutical Sciences*. (16th ed., Mack Publishing Co., Easton, Pa., U.S.A., 1980) ("*Remington's*"), at pages 1553 to 1584. Methods of making powders, and their composition are described at pages 1535 to 1552 of the reference. Methods of coating pharmaceutical dosage forms are described at pages 1585 to 1593 of *Remington's*.

For making dosage units, e.g. tablets, the use of conventional additives, e.g. fillers, colorants, polymeric binders and the like is contemplated. In general any pharmaceutically acceptable additive which does not interfere with the function of the active compounds can be used in the one or more of the compositions.

Suitable carriers with which the compositions can be administered include lactose, starch, cellulose derivatives and the like used in suitable amounts. Lactose is a preferred carrier. Mixtures of carriers can also be used.

A process of manufacturing the combination and contraceptive kit involves mixing predetermined quantities of progestogen with predetermined quantities of estrogen and converting the mixture into the first dosage units (e.g. by filling capsules or molding tablets with the mixture and any desired excipients); mixing predetermined quantities of progestogen with predetermined quantities of estrogen and converting that mixture into the second dosage units; and mixing predetermined quantities of progestogen with predetermined quantities of estrogen and converting that mixture into the third dosage units.

A preferred process of manufacturing the contraceptive product according to the invention involves incorporating the desired dosages of contraceptive steroid (i.e. progestogen with or without estrogen) into a tablet by known techniques. Tablets containing different amounts and types of contraceptive steroids may be of different colors, and kept in different portions of, for example, a blister pack. The package containing the dosage units will preferably contain 24 to 28 dosage units arranged sequentially therein. Preferably there will be 28 dosage units.

A preferred method of contraception using the invention comprises administering to a pre-menopausal fertile female:

for the first 7 to 9 days, separate first dosage units containing a progestogen at a daily dosage equivalent in progestogenic activity to 100 micrograms desogestrel and an estrogen at a daily dosage equivalent in estrogenic activity to 25 micrograms ethinyl estradiol;

for the next 7 to 9 days, second dosage units each containing a progestogen at a daily dosage equivalent in progestogenic activity to 125 micrograms desogestrel and an estrogen at a daily dosage equivalent in estrogenic activity to 20 micrograms ethinyl estradiol;

for the next 7 to 9 days, third dosage units, each containing a progestogen at a daily dosage equivalent in progestogenic activity to 150 micrograms desogestrel and an estrogen at a daily dosage equivalent in estrogenic activity to 20 micrograms ethinyl estradiol; and for the next 4 days and to complete the regimen, either a "pill-free" period, dosage units containing no contraceptive steroid, or dosage units containing a progestogen at a daily dosage equivalent in progestogenic activity to 25 to 35 micrograms desogestrel. The first, second, and third dosage units are administered for a total of 24 days. After the completion of a regimen, the regimen is repeated for as long as contraception is desired. One or more dosage units may contain an iron salt (e.g 75 mg of ferrous fumarate) if desired.

A preferred regimen is administered to a female of child bearing age at the following times over a 28 day period:

(a) for 8 days a composition containing 25 ethinyl estradiol and 100 $\mu$g desogestrel or equivalent amount of other progestogen;

(b) for 8 days a composition containing 20 $\mu$g ethinyl estradiol and 125 $\mu$g desogestrel or equivalent amount of other progestogen;

(c) for 8 days a composition containing 20 $\mu$g ethinyl estradiol and 150 $\mu$g desogestrel or equivalent amount of other progestogen; and (d) for 4 days a composition containing 25 to 35 $\mu$g desogestrel or equivalent amount of other progestogen.

The invention is further explained by the following illustrative EXAMPLES.

EXAMPLE I

Compositions of tablets:
A. In the first phase: (8 tablets)

| Compound | Amount (mg/tablet) |
| --- | --- |
| ethinyl estradiol | 0.025 |
| desogestrel | 0.100 |
| potato starch | 8.000 |
| polyvinyl pyrrolidone | 2.400 |
| stearic acid | 0.800 |
| silica | 0.800 |
| dl-α-tocopherol | 0.080 |
| lactose | qsad 80.000 |

B. In the second phase: (8 tablets)

| Compound | Amount (mg/tablet) |
| --- | --- |
| ethinyl estradiol | 0.020 |
| desogestrel | 0.125 |
| potato starch | 8.000 |
| polyvinyl pyrrolidone | 2.400 |
| stearic acid | 0.800 |
| silica | 0.800 |
| dl-α-tocopherol | 0.080 |
| lactose | qsad 80.000 |

C. In the third phase: (8 tablets)

| Compound | Amount (mg/tablet) |
| --- | --- |
| ethinyl estradiol | 0.020 |
| desogestrel | 0.150 |
| potato starch | 8.000 |
| polyvinyl pyrrolidone | 2.400 |
| stearic acid | 0.800 |
| silica | 0.800 |
| dl-α-tocopherol | 0.080 |
| lactose | qsad 80.000 |

D. In the fourth phase: (4 tablets)

| Compound | Amount (mg/tablet) |
| --- | --- |
| desogestrel | 0.030 |
| potato starch | 8.000 |
| polyvinyl pyrrolidone | 2.400 |
| stearic acid | 0.800 |
| silica | 0.800 |
| dl-α-tocopherol | 0.080 |
| lactose | qsad 80.000 |

EXAMPLE II

The same as in EXAMPLE I, except that the fourth phase is substituted with tablets having no steroid.

EXAMPLE III

Composition of tablets:
A. In the first phase: (8 tablets)

| Compound | Amount (mg/tablet) |
| --- | --- |
| ethinyl estradiol | 0.025 |
| 3-ketodesogestrel | 0.100 |
| potato starch | 8.000 |
| polyvinyl pyrrolidone | 2.400 |
| stearic acid | 0.800 |
| silica | 0.800 |
| dl-α-tocopherol | 0.080 |
| lactose | qsad 80.000 |

B. In the second phase: (8 tablets)

| Compound | Amount (mg/tablet) |
| --- | --- |
| ethinyl estradiol | 0.020 |
| 3-ketodesogestrel | 0.125 |
| potato starch | 8.000 |
| polyvinyl pyrrolidone | 2.400 |
| stearic acid | 0.800 |
| silica | 0.800 |
| dl-α-tocopherol | 0.080 |
| lactose | qsad 80.000 |

C. In the third phase: (8 tablets)

| Compound | Amount (mg/tablet) |
| --- | --- |
| ethinyl estradiol | 0.020 |
| 3-ketodesogestrel | 0.150 |
| potato starch | 8.000 |
| polyvinyl pyrrolidone | 2.400 |
| stearic acid | 0.800 |
| silica | 0.800 |
| dl-α-tocopherol | 0.080 |
| lactose | qsad 80.000 |

C. In the fourth phase: (4 tablets)

| Compound | Amount (mg/tablet) |
| --- | --- |
| 3-ketodesogestrel | 0.030 |
| potato starch | 8.000 |
| polyvinyl pyrrolidone | 2.400 |
| stearic acid | 0.800 |
| silica | 0.800 |
| dl-α-tocopherol | 0.080 |
| lactose | qsad 80.000 |

EXAMPLE IV

The same as in EXAMPLE III, except that the fourth phase is substituted with tablets having no steroid.

EXAMPLE V

Composition of tablets:
A. In the first phase: (8 tablets)

| Compound | Amount (mg/tablet) |
| --- | --- |
| micronized estradiol | 3.000 |
| 3-ketodesogestrel | 0.100 |
| potato starch | 8.000 |
| polyvinyl pyrrolidone | 2.400 |
| stearic acid | 0.800 |
| silica | 0.800 |
| dl-α-tocopherol | 0.080 |
| lactose | qsad 80.000 |

B. In the second phase: (8 tablets)

| Compound | Amount (mg/tablet) |
| --- | --- |
| micronized estradiol | 2.000 |
| 3-ketodesogestrel | 0.125 |
| potato starch | 8.000 |
| polyvinyl pyrrolidone | 2.400 |
| stearic acid | 0.800 |

-continued

| Compound | Amount (mg/tablet) |
|---|---|
| silica | 0.800 |
| dl-α-tocopherol | 0.080 |
| lactose | qsad 80.000 |

C. In the third phase: (8 tablets)

| Compound | Amount (mg/tablet) |
|---|---|
| micronized estradiol | 2.000 |
| 3-ketodesogestrel | 0.150 |
| potato starch | 8.000 |
| polyvinyl pyrrolidone | 2.400 |
| stearic acid | 0.800 |
| silica | 0.800 |
| dl-α-tocopherol | 0.080 |
| lactose | qsad 80.000 |

D. In the fourth phase: (4 tablets)

| Compound | Amount (mg/tablet) |
|---|---|
| 3-ketodesogestrel | 0.030 |
| potato starch | 8.000 |
| polyvinyl pyrrolidone | 2.400 |
| stearic acid | 0.800 |
| silica | 0.800 |
| dl-α-tocopherol | 0.080 |
| lactose | qsad 80.000 |

EXAMPLE V

The same as in EXAMPLE V, except that the fourth phase is substituted with tablets having no contraceptive steroid.

EXAMPLE VI

Composition of tablets:
A. In the first phase: (8 tablets)

| Compound | Amount (mg/tablet) |
|---|---|
| ethinyl estradiol | 0.025 |
| desogestrel | 0.075 |
| potato starch | 8.000 |
| polyvinyl pyrrolidone | 2.400 |
| stearic acid | 0.800 |
| silica | 0.800 |
| dl-α-tocopherol | 0.080 |
| lactose | qsad 80.000 |

B. In the second phase: (8 tablets)

| Compound | Amount (mg/tablet) |
|---|---|
| ethinyl estradiol | 0.020 |
| desogestrel | 0.125 |
| potato starch | 8.000 |
| polyvinyl pyrrolidone | 2.400 |
| stearic acid | 0.800 |
| silica | 0.800 |
| dl-α-tocopherol | 0.080 |
| lactose | qsad 80.000 |

C. In the third phase: (8 tablets)

| Compound | Amount (mg/tablet) |
|---|---|
| ethinyl estradiol | 0.020 |
| desogestrel | 0.150 |
| potato starch | 8.000 |
| polyvinyl pyrrolidone | 2.400 |
| stearic acid | 0.800 |
| silica | 0.800 |
| dl-α-tocopherol | 0.080 |
| lactose | qsad 80.000 |

D. In the fourth phase: (4 tablets)

| Compound | Amount (mg/tablet) |
|---|---|
| potato starch | 8.000 |
| polyvinyl pyrrolidone | 2.400 |
| stearic acid | 0.800 |
| silica | 0.800 |
| dl-α-tocopherol | 0.080 |
| lactose | qsad 80.000 |

What is claimed is:

1. A multiphasic combination contraceptive kit comprising three phases, said three phases consisting of 24 daily sequential dosage units with:
   a first phase comprising from 7 to 9 separate first dosage units, said first dosage units comprising progestogen at a dosage equivalent in progestogenic activity to 75–100 μg desogestrel, estrogen at a dosage equivalent in estrogenic activity to 25 μg ethinyl estradiol and a pharmaceutically acceptable carrier; a second phase of 7 to 9 second dosage units, each said second dosage unit comprising progestogen at a dosage equivalent in progestogenic activity to 100–125 μg desogestrel, estrogen at a dosage equivalent in estrogenic activity to 20 μg ethinyl estradiol and a pharmaceutically acceptable carrier; and
   a third phase of 7 to 9 third dosage units, each said third dosage units comprising progestogen at a dosage equivalent in progestogenic activity to 125–150 μg desogestrel, estrogen at a dosage equivalent in estrogenic activity to 20 μg ethinyl estradiol and a pharmaceutically acceptable carrier.

2. The multiphasic combination contraceptive kit of claim 1 further comprising a fourth phase comprising 4 additional dosage units containing no contraceptive steroid.

3. The multiphasic combination contraceptive kit of claim 1 further comprising a fourth phase comprising 4 additional dosage units comprising progestogen at dosage equivalent in progestogenic activity to 25 to 35 μg desogestrel.

4. The multiphasic combination contraceptive kit of claim 1, wherein said progestogen is selected from the group consisting of desogestrel, 3-ketodesogestrel, levonorgestrel, gestodene, and mixtures thereof.

5. The multiphasic combination and contraceptive kit of claim 4 wherein said progestogen is desogestrel or 3-ketodesogestrel.

6. The multiphasic combination and contraceptive kit of claim 5 wherein said progestogen is present in a quantity per dosage unit of 100 μg in the first dosage units, 125 μg in the second dosage units, and 150 μg in the third dosage units.

7. The multiphasic combination contraceptive kit of claim 1, wherein said estrogen is selected from the group consisting of 17β-estradiol, ethinyl estradiol, mestranol, 17-α-ethinyl estradiol 3-methylether, and mixtures thereof.

8. The multiphasic combination and contraceptive kit of claim 7 wherein said estrogen is 17β-estradiol or ethinyl estradiol.

9. A method of contraception in a female comprising orally administering in 28 day cycles to a premenopausal fertile female the following:

for a first 7 to 9 days, separate first dosage units comprising progestogen at a daily dosage equivalent in progestogenic activity to 75–100 µg desogestrel and estrogen at a daily dosage equivalent in estrogenic activity to 25 µg ethinyl estradiol;

for the next 7 to 9 days, second dosage units each second dosage unit comprising progestogen at a daily dosage equivalent in progestogenic activity to 101–125 µg desogestrel and estrogen at a daily dosage equivalent in estrogenic activity to 20 µg ethinyl estradiol;

for the next 7 to 9 days, third dosage units, each third dosage unit comprising progestogen at a daily dosage equivalent in progestogenic activity to 126–150 µg desogestrel and estrogen at a daily dosage equivalent in estrogenic activity to 20 µg ethinyl estradiol wherein said first, second and third dosage units are administered for a total of 24 days; and for the last 4 days of said 28 days, administering nothing, blank dosage units or dosage units comprising progestogen at a daily dosage equivalent in progestogenic activity to 25–35 µg desogestrel and no estrogen.

* * * * *